(12) United States Patent
Resnick

(10) Patent No.: US 6,388,139 B1
(45) Date of Patent: May 14, 2002

(54) PRODUCTION OF PERFLUORO (ALKYL VINYL) ETHERS

(75) Inventor: Paul Raphael Resnick, Cary, NC (US)

(73) Assignee: E. I. du Pont de Nemours and Company, Wilmington, DE (US)

(*) Notice: Subject to any disclaimer, the term of this patent is extended or adjusted under 35 U.S.C. 154(b) by 0 days.

(21) Appl. No.: 09/177,152

(22) Filed: Oct. 22, 1998

Related U.S. Application Data

(60) Provisional application No. 60/064,494, filed on Nov. 5, 1997.

(51) Int. Cl.[7] .......................... B01J 23/36; C07C 315/04
(52) U.S. Cl. .......................................................... 568/32
(58) Field of Search .................. 568/685, 682, 568/348, 669, 615, 616, 621, 674, 32; 560/227; 562/825

(56) References Cited

U.S. PATENT DOCUMENTS

| | | | |
|---|---|---|---|
| 4,275,226 A | * | 6/1981 | Yamabe et al. ............. 560/183 |
| 4,474,998 A | | 10/1984 | Uschold .................... 568/615 |
| 4,962,282 A | | 10/1990 | Marraccini et al. ......... 562/825 |
| 5,350,497 A | | 9/1994 | Hung et al. ............. 204/157.92 |
| 5,449,825 A | * | 9/1995 | Ishibe et al. ................ 562/851 |
| 5,679,851 A | | 10/1997 | Saito et al. ................. 564/136 |

FOREIGN PATENT DOCUMENTS

| | | | |
|---|---|---|---|
| EP | 0 201 871 | 7/1986 | ........... C07C/43/12 |

OTHER PUBLICATIONS

M. Hudlicky, Chemistry of Organic Fluorine Compounds, Ellis Norwood, New York, (1992) pp. 483–484.

\* cited by examiner

Primary Examiner—Rosalynd Keys

(57) ABSTRACT

A good yield, high reaction rate process is disclosed for the production of perfluoro(alkyl vinyl ethers). The process involves elimination of halogen, preferably chlorine, from carbon atoms $\alpha$ and $\beta$ to an ether oxygen in an $\alpha,\beta$-dihaloperfluoro ether wherein the $\alpha,\beta$-dihaloperfluoro ether is allowed to react with zero valent zinc in a pyrrolidinone solvent. More particularly, the inventive process relates to high yield production of $CF_2=CFOCF_2CF_2SO_2F$ from $CF_2ClCFClOCF_2CF_2SO_2F$ wherein $CF_2ClCFClOCF_2CF_2SO_2F$ is allowed to react with zero valent zinc in the presence of N-methyl-2-pyrrolidinone.

13 Claims, No Drawings

PRODUCTION OF PERFLUORO (ALKYL VINYL) ETHERS

RELATED APPLICATIONS

This application claims benefit of U.S. Provisional Application No. 60/064,494, filed Nov. 5, 1997.

FIELD OF INVENTION

This invention relates to the production of perfluoro(alkyl vinyl ethers) ethers from $\alpha,\beta$-dihaloperfluoro ethers by the elimination of halogen from carbon atoms $\alpha$ and $\beta$ to an ether oxygen.

BACKGROUND OF THE INVENTION

Perfluoro(alkyl vinyl ethers) are monomers that are widely used in the manufacture of commercial fluoropolymers. A variety of such fluoropolymers are sold by E. I. du Pont de Nemours and Company under the trademark Teflon® PFA. Perfluoro(alkyl vinyl ethers) can be made by various synthetic routes, but not all routes are suitable for all ethers. In some cases certain ethers can only be synthesized by certain methods, in other cases, reactions are sluggish or incomplete, yields are low, or undesirable byproducts are produced. To overcome these disadvantages, improved synthetic methods are needed.

It is known in organic chemistry that carbon-carbon double bonds can be formed by the elimination of vicinal dihalides (chloride, bromide, or iodide) by treatment with reducing agents such as zinc or magnesium. This synthetic technique has been extended to fluorocarbons, as can be seen by reference to M. Hudlicky, Chemistry of Organic Fluorine Compounds, Ellis Norwood, N.Y., (1992) pp.483–484. This technique has been further extended to the synthesis of perfluoro(alkyl vinyl ethers) by the elimination of halogen from carbon atoms $\alpha$ and $\beta$ to an ether oxygen, as in U.S. Pat. Nos. 4,474,998, 5,350,497 and 5,679,851, and European Patent 0 201 871. These patents teach the use of diglyme, dimethyl formamide (DMF), dioxane, and dimethyl sulfoxide (DMSO), respectively. The corresponding yields are 27%, 40–68%, 85–89%, and 90%. Dehalogenation in dioxane, though in good yield, was carried out at reflux (100° C.). For making some perfluoro(alkyl vinyl ethers), reactions in the solvents taught by the references do not consistently proceed at reasonable rates at the low temperatures desirable to minimize side reactions.

SUMMARY OF THE INVENTION

The present invention provides a process for the production in good yields and at consistently high reaction rates of perfluoro(alkyl vinyl ethers) from a $\alpha,\beta$-dihaloperfluoro ethers by the elimination of halogen from carbon atoms $\alpha$ and $\beta$ to an ether oxygen. In accordance with the present invention, a process is provided for producing perfluoro (alkyl vinyl ethers) represented by the formula A—CF=CF—O—B comprising the steps of contacting at least one $\alpha,\beta$-dihaloperfluoro ether represented by the formula A—CFX—CFX—O—B with zero valent zinc in the presence of a pyrrolidinone solvent to form a first mixture comprising perfluoro(alkyl vinyl ether) and recovering the perfluoro(alkyl vinyl ether) from the first mixture. In the formulas above:

X is selected from the halogens chlorine, bromine and iodine. X is preferably chlorine.

A is selected from fluorine and normal and branched chain perfluoroalkyl radicals, and B is selected from normal and branched chain perfluoroalkyl radicals. In both A and B, the perfluoroalkyl radicals can contain oxygen and sulfur heteroatoms configured in ether, ester, ketone, and sulfonyl fluoride functional groups. Furthermore, A and B can be bonded together forming a ring. Preferably, A is fluorine and B is selected from perfluoroalkyl radicals containing oxygen and sulfur heteroatoms configured in ether and sulfonyl fluoride functional groups. More preferably, the $\alpha,\beta$-dihaloperfluoro ether is selected from $CF_2XCFXOCF_2CF_2SO_2F$ and cyclo-(—OCFXCFXOC $(CF_3)_2$—) and the perfluoro(alkyl vinyl ether) is selected from $CF_2$=$CFOCF_2CF_2SO_2F$ and cyclo-(—OCF=CFOC $(CF_3)_2$—). In the most preferred embodiment, the $\alpha,\beta$-dihaloperfluoro ether is $CF_2ClCFClOCF_2CF_2SO_2F$ and the perfluoro(alkyl vinyl ether) is $CF_2$=$CFOCF_2CF_2SO_2F$.

DETAILED DESCRIPTION $\alpha,\beta$-Dihaloperfluoro ethers for use in accordance with the present invention can be prepared by any conventional processes known in the art. For example, preparation of $\alpha,\beta$-dihaloperfluoro ether of the formula $CF_2XCFXOCF_2CF_2SO_2F$, where X is chlorine, is disclosed in U.S. Pat. No. 4,962,282. Preparation of $\alpha,\beta$-dihaloperfluoro ethers of the formula cyclo-(—OCFXCFXOC $(CF_3)_2$—) is disclosed in U.S. Pat. No. 4,535,175. The $\alpha,\beta$-dihaloperfluoro ethers are preferably at least 95 wt % pure, and more preferably at least 99.5 wt % pure when employing in the present process. Such purity can be obtained through conventional processes known in the art, such as reduced pressure fractional distillation.

The contacting of the $\alpha,\beta$-dihaloperfluoro ethers with zero valent zinc in the presence of pyrrolidinone solvent is preferably carried out at temperatures of about 0° C. to 100° C., more preferably at about 10° C. to about 50° C. Most preferably, the contacting is performed at about 20° C. to about 40° C. It has been discovered that the invention can provide good reaction rates at lower temperature which decreases undesired side reactions. The temperatures for the contacting described above refer to the period during which the bulk of the $\alpha,\beta$-dihaloperfluoro ethers are reacted. During the separation of the perfluoro(alkyl vinyl ether) product such as by distillation, some minor amount of unreacted $\alpha,\beta$-dihaloperfluoro ethers, if present, may be exposed to higher temperatures. The contacting of $\alpha,\beta$-dihaloperfluoro ethers with zero valent zinc preferably occurs in the absence of water and oxygen. Preferably, the contacting occurs in the presence of bromine ($Br_2$). It is believed that bromine activates the zinc surface resulting in reactions with shorter induction periods and higher conversion and yield of perfluoro(alkyl vinyl ether) from $\alpha,\beta$-dihaloperfluoro ether. By induction period is meant the period of time between first contact of $\alpha,\beta$-dihaloperfluoro ether and zinc, and the generation of a reaction exotherm and sustainable reaction.

Zero valent zinc is preferably finely divided to provide maximal surface area, such as 99.998% 100 mesh zinc powder produced by Aldrich Chemical Co. Inc., Milwaukee, Wis., USA. Such zinc powder may be used as is, or may be activated by processes known in the art which remove surface oxide coatings, such as contact with strong acid such as aqueous HCl followed by rinsing and drying.

When other solvents commonly used in dehalogenation are used such as ethers, alcohols, and organic acids, reaction rates are generally low. The reaction carried out in the presence of a solvent of the pyrrolidinone family consistently gives good yields at good reaction rates. Other solvents may be present provided they do not interfere with the dehalogenation reaction.

The pyrrolidinone solvent preferably is selected from the N-alkyl-2-pyrrolidinones, where the alkyl group may be substituted, and preferably, N-methyl-2-pyrrolidinone (also known as 1-methyl-2-pyrrolidinone). Suitable N-methyl-2-pyrrolidinone is commercially available such as 99+%, A.C.S reagent grade 1-methyl-2-pyrrolidinone offered by Aldrich Chemical Co. Inc., Milwaukee, Wis., USA. Other possible pyrrolidinone solvents available are N-ethyl-2-pyrrolidinone, N-isopropyl-2-pyrrolidinone, N-(2-hydroxyethyl)-2-pyrrolidinone, N-cyclohexyl-2-pyrrolidinone, N-octyl-2-pyrrolidinone, and N-dodecyl-2-pyrrolidinone. The solvent is preferably free of water. Prior to employing in the present process, the solvent may be dried to remove water by conventional drying agents such as molecular sieves or metal hydrides such as $CaH_2$ and may be further purified by distillation.

The recovering of perfluoro(alkyl vinyl ether) from the first mixture may be carried out by extraction or distillation. Preferably, distillation of the first mixture is employed and more preferably, reduced pressure distillation of the first mixture is employed which affords high yields of perfluoro (alkyl vinyl ether) as distillate.

EXAMPLES

The following examples are offered for the purpose of further illustrating the process of the present invention and are by no means intended to be limiting.

Example 1
Preparation of $CF_2=CFOCF_2CF_2SO_2F$ in N-methyl-2-pyrrolidinone (NMP)

A 125 ml, three necked, round bottom flask is fitted with a magnetic stirrer, thermometer, 50 ml pressure equalizing dropping funnel and a simple distillation head topped by a dry ice cooled cold finger trap. The apparatus is blanketed with dry nitrogen and dried by heating with a free flame and sweeping with nitrogen.

The flask is charged with 9.8 g zinc dust (9.8/65.4=0.150 gram atom) and 50 ml N-methyl-2-pyrrolidinone. The reaction mixture is stirred at ambient temperature and 1.0 g bromine (1.0/160=0.00625 mole) is added. An exothermic reaction occurs and the temperature of the reaction mixture rises from 25° C. to 47°. The flask is cooled to 29° C. and 36.7 g $CF_2ClCFClOCF_2CF_2SO_2F$ (36.7/351=0.1046 mole) is added dropwise. An immediate exothermic reaction occurs and the flask is cooled with a cold water bath. The $CF_2ClCFClOCF_2CF_2SO_2F$ is added dropwise over 15 minutes keeping the temperature of the reaction mixture below 35° C.

After addition of $CF_2ClCFClOCF_2CF_2SO_2F$ is completed, the reaction mixture is heated slowly over 80 minutes to 85° C. and a colorless material is distilled starting at 75° C. The pot (reaction mixture) temperature is then slowly raised to 125° C. and then cooled to 30° C. once distillation of colorless distillate from the pot ceases. The colorless distillate weighs 21.1 g and is washed with 50 ml ice water to give 20.4 g of colorless product. Gas chromatography shows the product to be 98.7% $CF_2=CFOCF_2CF_2SO_2F$ by comparison with a known sample. The infrared and fluorine nuclear magnetic resonance spectra are identical to those obtained from a known sample of $CF_2=CFOCF_2CF_2SO_2F$. The colorless distillate isolated corresponds to a $(20.4)(0.987)/(0.1046)(280)=68.8\%$ yield of $CF_2=CFOCF_2CF_2SO_2F$.

The reaction mixture is then vacuum distilled at 25 mm Hg to give 30 ml of a second distillate boiling at 100° C. The final pot temperature is 185° C. The second distillate is colorless for the first 20 ml and then becomes slightly yellow. The yellow material is identified as N-methyl-2-pyrrolidinone solvent. This recovered solvent is used in subsequent dechlorination reactions with no adverse effects.

The dry ice cooled cold finger trap contains 4.0 g of colorless liquid which is washed with ice water to give 3.7 g colorless liquid containing 88.8% $CF_2=CFOCF_2CF_2SO_2F$ as well as 3.4% starting material and 6.6% of the partially reduced product $CF_2ClCFHOCF_2CF_2SO_2F$. The material corresponds to an additional $(3.7)(0.888)/(0.1046)(280)=11.2\%$ $CF_2=CFOCF_2CF_2SO_2F$ or an overall $CF_2=CFOCF_2CF_2SO_2F$ yield of 80.0%.

The pot residue is too thick to stir at ambient temperature after addition of 25 ml water but can be easily stirred when heated to 50° C. The resulting mixture consists of a dark brown liquid and a small amount of a gray solid.

Comparative Example 2
Preparation of $CF_2=CFOCF_2CF_2SO_2F$ in Ethyl Carbitol In the same equipment and using the procedures described in Example 1, 9.8 g (0.150 gram atom) of zinc dust and 50 ml ethyl carbitol is charged to the flask. 1 g (0.00625 mole) of bromine is added. After the exotherm, the flask was cooled and 35.1 g (0.10 mole) of $CF_2ClCFClOCF_2CF_2SO_2F$ is added dropwise. Only a slight exotherm is observed. Distillation and analysis show that the crude product is 40% $CF_2=CFOCF_2CF_2SO_2F$ and 45% unconverted starting material, $CF_2ClCFClOCF_2CF_2SO_2F$. The yield of $CF_2=CFOCF_2CF_2SO_2F$ is 23%.

Comparative Examples 3–6
Preparation of $CF_2=CFOCF_2CF_2SO_2F$ in Dimethyl Formamide (DMF)

In the same equipment and using the procedures described in Example 1, dimethyl formamide (DMF) is used as the solvent. In each case 0.1 mole of $CF_2ClCFClOCF_2CF_2SO_2F$ is charged. Table 1 summarizes the results. Reactions are generally slow. At the end of the reaction, little unreacted starting material remains.

TABLE 1

| Example | Bromine (g) | Zinc (g) | Yield (%) | Reaction Rate |
|---------|-------------|----------|-----------|---------------|
| 3 | 1 | 9.8 | 70 | Rapid |
| 4 | 1 | 9.8 | 71 | Sluggish |
| 5 | 1 | 14.7 | 72 | Sluggish |
| 6 | 1 | 14.7 | 61 | Sluggish |

Comparative Example 7
Preparation of $CF_2=CFOCF_2CF_2SO_2F$ in Diglyme

In the same equipment and using the procedures described in Example 1, and charging 0.1 mole of $CF_2ClCFClOCF_2CF_2SO_2F$, diglyme is used as the solvent. Table 2 summarizes the results.

TABLE 2

| Example | Bromine (g) | Zinc (g) | Yield (%) | Reaction Rate |
|---|---|---|---|---|
| 7 | 1 | 14.7 | 13 | Very slow |

Comparative Example 8

Preparation of $CF_2=CFOCF_2CF_2SO_2F$ in Acetic Acid

In the same equipment and using the procedures described in Example 1 (except that bromine is not used), and charging 0.1 mole of $CF_2ClCFClOCF_2CF_2SO_2F$, acetic acid is used as the solvent. Table 3 summarizes the results.

TABLE 3

| Example | Bromine (g) | Zinc (g) | Yield (%) | Reaction Rate |
|---|---|---|---|---|
| 8 | 0 | 9.8 | 59 | Very slow |

Examples 9 to 14

Preparation of $CF_2=CFOCF_2CF_2SO_2F$ in N-methyl-2-pyrrolidinone (NMP)

In the same equipment and using the procedures described in Example 1, and charging 0.1 mole of $CF_2ClCFClOCF_2CF_2SO_2F$, N-methyl-2-pyrrolidinone is used as the solvent. Table 4 summarizes the results. The reactions are consistently rapid.

TABLE 4

| Example | Bromine (g) | Zinc (g) | Yield (%) | Reaction Rate |
|---|---|---|---|---|
| 9 | 1 | 14.7 | 76 | Rapid |
| 10 | 1 | 14.7 | 81 | Rapid |
| 11 | 1 | 9.8 | 82 | Rapid |
| 12 | 1 | 9.8 | 81 | Rapid |
| 13 | 1 | 9.8 | 68 | Rapid |
| 14 | 1 | 9.8 | 68 | Rapid |

Examples 15 to 16

Preparation of $CF_2=CFOCF_2CF_2SO_2F$ in N-methyl-2-pyrrolidinone (NMP)

In the same equipment and using the procedures described in Example 1, and charging 0.1 mole of $CF_2ClCFClOCF_2CF_2SO_2F$, N-methyl-2-pyrrolidinone is used as the solvent. 1 g of cupric iodide is added with the zinc dust. Table 5 summarizes the results. The reactions are consistently rapid.

TABLE 5

| Example | Bromine (g) | Zinc (g) | Yield (%) | Reaction Rate |
|---|---|---|---|---|
| 15 | 1.2 | 9.8 | 80 | Rapid |
| 16 | 1 | 9.8 | 77 | Rapid |

What is claimed is:

1. A process for producing perfluoro(alkyl vinyl ether) represented by the formula A—CF=CF—O—B, comprising the steps of:
   contacting at least one α,β-dihaloperfluoro ether represented by the formula A—CFX—CFX—O—B with zero valent zinc in the presence of a pyrrolidinone solvent to form a first mixture comprising perfluorovinyl ether, and
   recovering the perfluoro(alkyl vinyl ether) from the first mixture,
   wherein:
     X is selected from the group consisting of chlorine, bromine, or iodine,
     A is selected from the group consisting of fluorine and normal and branched chain perfluoroalkyl radicals, and B is selected from the group consisting of normal and branched chain perfluoroalkyl radicals, wherein A and B can contain oxygen and sulfur heteroatoms configured in functional groups selected from ether, ester, ketone, and sulfonyl fluoride, and wherein A and B can be bonded together forming a ring.

2. The process of claim 1 wherein X is chlorine.

3. The process of claim 1 wherein A is fluorine and B is selected from the group consisting of perfluoroalkyl radicals containing oxygen and sulfur heteroatoms configured in functional groups selected from ether and sulfonyl fluoride.

4. The process of claim 1 wherein the α,β-dihaloperfluoro ether is selected from the group consisting of $CF_2XCFXOCF_2CF_2SO_2F$ and cyclo-(—OCFXCFXOC$(CF_3)_2$—) and the perfluoro(alkyl vinyl ether) is selected from $CF_2=CFOCF_2CF_2SO_2F$ and cyclo-(—OCF=CFOC$(CF_3)_2$—), wherein X is selected from the group consisting of chlorine, bromine and iodine.

5. The process of claim 1 wherein the α,β-dihaloperfluoro ether comprises $CF_2ClCFClOCF_2CF_2SO_2F$ and the perfluoro(alkyl vinyl ether) comprises $CF_2=CFOCF_2CF_2SO_2F$.

6. The process of claim 1 wherein said contacting is carried out at about 0° C. to about 100° C.

7. The process of claim 1 wherein said contacting is carried out at about 10° C. to about 50° C.

8. The process of claim 1 wherein said contacting is carried out at about 20° C. to about 40° C.

9. The process of claim 1 further comprising performing said contacting in the presence of bromine.

10. The process of claim 1 wherein said pyrrolidinone solvent is selected from the group consisting of N-alkyl-2-pyrrolidinones.

11. The process of claim 10 wherein the pyrrolidinone solvent comprises N-methyl-2-pyrrolidinone.

12. The process of claim 1 wherein said recovering comprises extraction of the perfluoro(alkyl vinyl ether) from the first mixture.

13. The process of claim 1 wherein said recovering comprises distillation of the perfluoro(alkyl vinyl ether) from the first mixture.

* * * * *